United States Patent [19]

Makari

[11] Patent Number: 4,783,313

[45] Date of Patent: Nov. 8, 1988

[54] ENHANCING BODY DEFENSE MECHANISMS

[76] Inventor: Jack G. Makari, 88 Everett Rd., Demarest, N.J. 07627

[21] Appl. No.: 118,275

[22] Filed: Nov. 6, 1987

Related U.S. Application Data

[60] Division of Ser. No. 888,261, Jul. 17, 1986, Pat. No. 4,705,677, which is a continuation-in-part of Ser. No. 793,294, May 3, 1977, abandoned, which is a continuation-in-part of Ser. No. 159,473, Jul. 2, 1971, abandoned, which is a continuation-in-part of Ser. No. 535,364, Mar. 18, 1966, abandoned, which is a continuation-in-part of Ser. No. 421,683, Dec. 28, 1964, abandoned, which is a continuation-in-part of Ser. No. 75,454, Aug. 6, 1959, abandoned.

[51] Int. Cl.$^4$ ............................................. A61K 43/00
[52] U.S. Cl. .................................. 424/1.1; 424/85.91; 424/88; 424/95; 514/2; 514/8; 514/44
[58] Field of Search ...................... 424/1.1, 85, 88, 95; 514/2, 8, 44

[56] References Cited

PUBLICATIONS

Makari–American Geriatrics Soc. J. vol. 8, Jan. 1970 pp. 16–29.
Makari–Bacterial Proc. 1963 p. M66.
Rajam et al–Chem. Abst. vol. 54(1960) p. 6938i.

*Primary Examiner*—Sam Rosen
*Attorney, Agent, or Firm*—Darby & Darby

[57] ABSTRACT

Disclosed is a method of providing immuno-prophylaxis as well as malignant tumor immuno-therapy by administering a malignant-tumor-immunization and recession-provoking antigenic agent of malignant tumor tissue source to a living subject in an effective dosage and regimen to develop a sufficiently high level of defense against malignant tumor incipience, or to retard such tumor development and/or provoke its recession.

The malignant-tumor-immunization and recession-provoking antigenic agent or tumor tissue source is a combination of:

(a) the tritiated form of glycoprotein polysaccharide-like-antigenic substance (TPS) obtained by removing lipids and protein from a differential centrifugation sediment of a saline suspension of the mitochondrial fraction of cancer tissue, e.g. from carcinoma, fibrosarcoma, lymphoma, or melanoma: and (b) deoxyribonucleic acid (DNA) derived from the nuclear fraction of malignant tumor tissue; or (c) the untritiated form of the glycoprotein polysaccharide-like antigenic substance (TPS) described in (a) above.

3 Claims, No Drawings

ENHANCING BODY DEFENSE MECHANISMS

This application is a division, of application Ser. No. 888,261 filed July 17, 1986, now U.S. Pat. No. 4,705,677, which was a continuation-in-part of my copending application Ser. No. 793,294 filed May 3, 1977, now abandoned which is a continuation-in-part of my then copending application Ser. No. 159,473 filed July 2, 1971, (now abandoned), which is a continuation-in-part of my then copending application Ser. No. 535,364 filed Mar. 18, 1966 (now abandoned), which in turn is a continuation-in-part of and was copending with my application Ser. No. 421,683 filed Dec. 28, 1964 (now abandoned), which in turn is a continuation-in-part of my then copending application Ser. No. 75,454 filed on Aug. 6, 1959 (now abandoned).

FIELD OF THE INVENTION

This invention relates to a method of enhancing the defense mechanisms in the body of a living subject, e.g. mammal or fowl, against the incipience or development of malignant tumors or to cause and promote the recession of an existing malignant tumor at any of its stages.

SUMMARY OF THE INVENTION

The present invention comprises malignant tumor immuno-prophylaxis as well as malignant tumor immuno-therapy by administering a malignant-tumor-immunization and recession-provoking antigenic agent of malignant tumor tissue source to a living subject in an effective dosage and regimen to develop a sufficiently high level of defense against malignant tumor incipience, or to retard such tumor development and/or provoke its recession. The initial early stage of the tumor is called its incipient-stage or an incipient-tumor to distinguish from a tumor in its intermediate or later stage.

The malignant-tumor-immunization and recession-provoking antigenic agent of tumor tissue source is a combination of:

(a) the tritiated form of glycoprotein polysaccharide-like-antigenic substance (TPS) obtained by removing lipids and protein from a differential centrifugation sediment of a saline suspension of the mitochondrial fraction of cancer tissue, e.g. from carcinoma, fibrosarcoma, lymphoma, or melanoma, as more fully described below; and (b) deoxyribonucleic acid (DNA) derived from the nuclear fraction of malignant tumor tissue; or (c) the untritiated form of the glycoprotein polysaccharide-like antigenic substance (TPS) described in (a) above.

DETAILED DESCRIPTION

TPS is essentially a glycoprotein polysaccharide-like antigenic substance which readily disperses in water and aqueous saline (usually sodium chloride, sometimes potassium chloride) solutions to form a stable, non-dialyzable solution, is stable to boiling in water or in aqueous saline solutions, inert to alkali and to isotonic phosphate buffered saline solution, precipitated from aqueous medium by isopropanol and insoluble in isopropanol, ether, chloroform, and butanol, withstands autoclaving at 250° F. and at 20 lbs. per square inch for at least 30 minutes and retains its activity after autoclaving even to 6 hours, gives a positive Molisch test and a negative Dische test, and on hydrolysis with dilute sulfuric acid at about 100 C. followed by deionization, yields a hydrolysate containing identifiable sugars, and on finite analysis shows trace amounts of amino acids typical of N-glycoproteins; and which when admixed in an aqueous vehicle with blood serum, and thereafter injected intradermally into a reactive human subject, produces an erythema about the injection site.

A. Preparation of Initial Antigenic Substance

The preparation of TPS involves first the derivation of an initial glycoprotein-polysaccharide-like antigenic substance from cancer cells. Essentially, this initial antigenic substance comprises the mitochondrial fraction of the cells from which lipids and proteins have been removed as described below. The antigenic substance can be manufactured from animal or human cancerous tissues although human tissue is preferred since it has fewer viruses. Generally speaking, primary cancers or cancer recurrences at the primary site are preferred although it is believed that metastatic cancers could be used as well. Moreover, all forms of cancer can be used, but, in accordance with the preferred embodiment, the antigenic substances are derived from carcinoma (TPS 1), sarcoma (TPS 2) and lymphoma (TPS 3).

In deriving TPS 1, carcinoma of the lung is preferred since it has relatively little fat and other extraneous tissues. It currently appears that any form of sarcoma or lymphoma can be used. The process as described in the following is the same for each of TPS 1, TPS 2 and TPS 3.

1. Separation of Mitochondrial Fraction

After the selected cancerous tissue is obtained (for example by resection) from a human harboring the cancer, it is examined microscopically to verify the type of cancer. It is then disintegrated to rupture the cell membranes so that the mitochondrial fraction of the cells can be separated from the cell membranes and nuclei.

The cancer cells may be disintegrated as indicated above by grinding, and advantageously homogenizing, the selected tissue in 0.1 molar saline (i.e. sodium chloride) solution or distilled water to provide a suitably centrifugable material, preferably an homogenate (referred to hereinafter for purposes of discussion) of from 15 to 50% solids by weight, optimally of about 20% (e.g., 4 ml saline to 1 g tissue). The homogenate is centrifuged in a refrigerated centrifuge at a temperature of about 0°–5° C. at a sufficient speed to throw down the cell membranes and nuclei. For example, the homogenate may be centrifuged at a speed of of about 1000 to about 3500 r.p.m. (equivalent to 110 to 1200 g) for from about 2 minutes to about 30 minutes and beneficially from about 15 to 20 minutes. The sediment is discarded.

The supernatant liquid is then centrifuged at from about 9000 to about 15,000 (equivalent to 8500 to 26,000 g), and optimally at about 10,000, r.p.m. (equivalent to 10,000 g), for from about 10 to 30 minutes to cause the sedimentation of the mitochondrial fraction.

These sedimentations can be carried out at any temperature below that at which enzymatic action occurs, i.e., between about zero and 25° C. and optimally from zero to about 5° C.

2. Glycoprotein-Polysaccharide Isolation

The mitochondrial fraction contains lipids and proteins which tend to reduce the specificity of the TPS as a cancer-detecting agent. Accordingly, it is desirable to isolate the glycoproteins and polysaccharides from the dispersion. This can be done by known processes of the type used to extract pneumococcal polysaccharides from bacteria. Two such processes are described in the following sections 2.(a) and (b).

a. Preferred Method

The mitochondrial sediment is dispersed in a physiological saline solution to its original volume. The mitochondrial dispersion is then mixed with from about 0.1 to about 5 times its volume (optimally about 0.5 volume) of an organic lipid solvent, e.g. diethyl ether. The mixture is vigorously agitated for a sufficient time to dissolve the lipids, for example, from about 5 to about 10 minutes. The mixture then is allowed to stand to separate into its ether and aqueous phases. The ether layer (containing the lipids) is discarded. The procedure can be repeated several times to ensure removal of the lipids.

Aqueous alkali is added to the drawn off aqueous phase to raise its pH to above 7 and the temperature is raised to from about 80° C. to boiling for a time sufficient to hydrolyze the proteins. For example, sodium hydroxide solution may be admixed to the aqueous phase in an amount sufficient to provide alkali corresponding to from about 10% to about 15% by volume, calculated as 2N NaOH, and the mixture heated in a water bath at 100° C. for about 30 minutes.

The mixture containing the hydrolyzed protein is then cooled and dialyzed through a membrane which will pass the low molecular weight compounds and retain the high molecular weight compounds of the hydrolysate. Such a membrane may have a pore size which excludes compounds having a molecular weight of 3500 or more. The time of dialysis may be about 2 hours at a conveniently safe temperature, for example, from zero to about 25° C. and optimally at from about freezing to about 5° C. The mixture may be dialyzed against distilled water or advantageously a buffered phosphate saline solution (e.g. at pH 6.8 and composed of 0.81 g., i.e. gram, $Na_2HPO_4$, 1.04 g. $KH_2PO_4$, 6.8 g. NaCl, in 1 liter distilled water.)

The high molecular weight dialysis residue contains the initial glycoprotein polysaccharide-like antigenic substance. The residue is shaken or stirred together vigorously in from about 0.25 to about 5 volumes, and optimally about equal volumes, of a protein-denaturing agent (for example, chloroform containing 2% n-octanol) in which the protein and the glycoprotein-polysaccharide-like antigenic substances are insoluble, for a sufficient time (from about 1 to 15 minutes, optimally about 10 minutes) to denature the protein. The mixture is then separated into chloroform and aqueous layers, advantageously by centrifugation at a speed sufficient to expedite phase separation, for example, about 1000 r.p.m. (or less) to about 3000 r.p.m., for about 10 to 30 minutes. The denatured protein collects at the interface of the two layers and the protein and heavier chloroform layer are discarded. The chloroform extraction is repeated as often as necessary until two consecutive separations show no protein at the interface.

The clear aqueous phase contains the desired initial glycoprotein-polysaccharide-like antigenic substance. The Molisch test for sugar and the Dische test for nucleic acids may be conducted as described in Kabat and Mayer "Experimental Immunochemistry", 2nd edition, pages 526–527 and 553 respectively. These tests are not necessary but, if conducted, should be positive for the Molisch test and negative for the Dische test.

b. Alternate Method

An effective alternate method for isolating the initial glycoprotein-polysaccharide-like antigenic substance involves suspending the mitochondrial sediment from the high speed centrifuge in a buffer solution such as acetate buffer (e.g. 157.5 gm. of $NaC_2H_3O_2 3H_2O$ in 3 liters of distilled water) and adjusting the pH to about 6 with a compatible acid, e.g. glacial acetic acid. This suspension is frozen and ground, preferably slowly to avoid undue temperature rise, and thereafter heated merely enough to melt it. The ground suspension then is centrifuged at a speed of at least about 10,000, and preferably between about 15,000 and about 20,000 rpm.

The supernatant is withdrawn and the sediment discarded. Several volumes of a water-miscible precipitant for polysaccharides and glycoprotein-like substances, e.g. about 5 volumes of cold isopropanol, are admixed with the supernatant to precipitate the polysaccharides and glyco-protein-like substances. The precipitate is separated and the supernatant discarded.

This precipitate is dissolved in cold distilled water and the resulting turbid greenish solution is deproteinized by compatible deproteinization such as the Sevag method, Biochemische Zeitschrift, volume 273 (1934) page 319 (see Example 3).

This initial antigenic substance isolated in accordance with either of the above procedures disperses readily in water or aqueous saline solutions to give a stable, non-dialyzable solution at a molecular weight cutoff of 3500; is stable in 0.18 molar saline solutions at from about 0° to 5° C.; is precipitated from aqueous medium by isopropanol and insoluble in isopropanol; behaves like a glycoprotein (and so is called "glycoprotein-polysaccharide-like") giving a positive Molisch test and negative Dische test; on hydrolysis with dilute sulfuric acid at about 100° C., followed by de-ionization as with a cationic ion exchange resin such as 'Dowex-50', yields a hydrolysate containing identifiable sugars; and on finite analysis shows amounts of amino acids typical of glycoproteins.

B. Preparation of Purified TPS

If the initial antigenic substance contains any undesirable dialyzable substances (e.g. such as peptides), the solution should be dialyzed through a membrane having a molecular weight cutoff point of 3500, such as a cellulose acetate membrane, against water under suitable conditions for a time sufficient to dialyze out substantially completely the dialyzable substances, e.g. for about 1 to 2 days at from 5° to 22° C.

Then the product of this dialyzation or of the deproteinization treatment, if it did not need dialysis, can be further processed for storage such as by drying under conditions to preserve the integrity (i.e. the effectiveness for extended use) of the product, for example, by lyophilization. The initial antigenic substance may also be stored in liquid form at a temperature of 5° C. The product, if stored in lyophilized form, when ready for further processing, can be reconstituted in an aqueous buffered solution (with a buffer such as ammonium bicarbonate, ammonium formate, or pyridine acetate of pH range from 3 to 9 and optimally between 5 and 6). A volatilizable buffer (e.g. pyridine acetate) is preferred since it will disappear if the TPS is dried (e.g. by lyophilization) for purposes of storage.

The resulting buffer solution of the lyophilized material then is fed onto a properly prepared bed of chromatographic-type gel beads effective to enable chromatographically the retention of substances within a molecular weight range of, for example, from about 2500 to about 40,000 or more. Such beads may include 200 to 400 mesh (37 to 75 microns size) polyacrylamide (copolymer of acrylamide and N,N-methylene-bisacrylamide) beads such as Bio-Gel P-30 of Bio-Rad Laboratories, of Los Angeles, Calif., dextran gel beads (40 to 100 microns) such as Sephadex G-75 of Pharmacia Fine Chemicals, Inc. of 800 Cenntennial Avenue, Piscataway, N.J., or other equivalent materials.

After the buffered reconstituted solution has passed through the gel bed, the part of it retained in the bed is eluted with an eluate buffer solution of the same constitution as that used to dissolve the lyophilization product. The elution profile of the resulting column eluate solution is determined from a series of suitable small volume fractions collected as in a fraction collector, for example, (a) by the Lowrey Protein Method (O. H. Lowrey, Jr. Biolog. Chem. 1951, vol. 193, p. 265) or the Bio-Rad Protein Assay (Bio-Rad Laboratories, above) or (b) by monitoring the column effluent by an ultraviolet detector. Then the fractions exhibiting the highest effectiveness (i.e. cancer specificity), specifically those fractions found to correspond approximately to the middle third of the main broad peak of the elution profile, are pooled. These pooled fractions are what is referred to herein as TPS. The same procedure is used to make TPS 1, TPS 2 and TPS 3.

Each TPS (i.e. TPS 1, TPS 2 and TPS 3), in addition to exhibiting the properties of the initial glycoprotein polysaccharide-like antigenic substance, is optically active; forms white to amber powder when lyophilized; shows molecular weights from about 3500 to about 50,000 as determined by gel chromatography; remains stable for at least ten years when held at 5° C. in liquid form; is stable to autoclaving; and yields patterns typical of sugars and amino acids on analysis by nuclear magnetic resonance and by gas liquid chromatography.

In comparison to the initial antigenic substance, each TPS shows much less heterogeneity under iso-electric focusing, and one-half the optical density in ultraviolet absorbance (at 280 nm.). Under NMR examination, different molecular configurations of the sugars and amino acid moieties and a lesser amount of amino acid moieties were observed.

C. Preparation of 3H-TPS

While TPS indicates utility in its ordinary form obtained (as described above) from its malignant tumor tissue source, effectiveness is enhanced by treatment to provide TPS in a modified form, for example, (i) in so-called isotopic form, which is its tritiated form (briefly designated as $^3$H-TPS), or (ii) linked (as described further below) with a lipopolysaccharide (briefly designated LPS) to make more complete immunogens. $^3$H-TPS is obtained by treating the earlier described ordinary TPS with tritium, as by tritiating it by the Wilzbach procedure (J. Wilzbach, Journal of the American Chemical Society, Volume 79 (1957), page 1013 etc.) and as conducted by the New England Nuclear Corporation, in Boston, Mass.

$^3$H-TPS can be prepared from TPS obtained from any cancer tissue such as described above and also from mouse sarcoma 180. The latter is designated "$^3$H-TPS-sarcoma 180". $^3$H-TPS also can be prepared from TPS obtained from neoplastic tissue propogated in the laboratory, such as that from virus infected tissue culture cells, e.g. chicken leucosis virus propogated tissue cultures.

D. Preparation of Malignant Tumor Tissue DNA

The method of the present invention can also be carried out with a further modification wherein $^3$H-TPS is administered either simultaneously or at a somewhat later time with deoxyribonucleic acid obtained from the nuclear fraction (or including the cell walls) of malignant tumor tissue, and which may be designated "tumor tissue DNA", or if obtained from a specific malignant tumor tissue such as the sarcoma 180 of mice, then designated "DNA-sarcoma 180".

EXAMPLE 1

Malignant tumor tissue DNA was prepared by treating the sediment obtained from centrifugation of the cell-walls and nuclear fraction of the malignant tumor tissue at approximately 3000 r.p.m. with 'Freon' 113 in the ratio of 2 volumes Freon to 1 of sediment and 1 of physiological saline, for 5 minutes in a Virtis homogenizer at 15,000 r.p.m. with its homogenizing cup submerged in ice. The homogenate was then centrifuged at about 3000 r.p.m. for 5 minutes in a Lourde refrigerated centrifuge, and the aqueous layer separated and kept for later pooling.

The sediment/Freon mixture was then extracted with 1M sodium chloride, homogenized, and centrifuged; and the aqueous layer tested by the Dische reaction (Zeitschrift fur Mikrochemie, vol. 8 page 4, 1930). The procedure was repeated until no more DNA was extracted as indicated by a negative Dische reaction. All of the aqueous fractions which gave a positive Dische reaction were then pooled and repeatedly treated with Freon (1 volume Freon to 2 volumes aqueous fraction) until deproteinization was complete, i.e. until no further precipitate appeared at the interface.

The final aqueous phase was then concentrated by dialysis under pressure in a cellophane bag against distilled water at 5° C. overnight, followed by dialysis against 0.15M NaCl for 2 to 3 days until the desired DNA concentration was obtained, between 100 and 1000 µg (i.e. micrograms) per ml. The pH was adjusted with sodium hydroxide to 7.2. The final tumor tissue DNA solution was standardized, using the Dische reaction, against a standard made from commercial thymus DNA, and passed through a V ultrafilter of fritted glass before use.

No special attempt was made to separate any contaminating ribonucleic acid (RNA) or any polysaccharide which might have been associated with the foregoing DNA fraction. As the starting material was nuclear and cell wall fractions, contamination with cytoplasmic RNA was believed to be minimal. Proteins and lipids were removed by the foregoing treatment with Freon.

While the DNA can be obtained from mouse sarcoma tissue, DNA similarly obtained from other tumor tissue in mouse or from any other tumor tissue in other mammals or in fowl likewise can be used. So also, while the above described TPS is derived from a specific human malignant tumor tissue, TPS can be derived from any other human malignant tumor or from such tumor tissue from any other mammal or fowl.

E. Immunization and Immunotherapy Regimens

Combinations of $^3$H-TPS alone, tumor tissue DNA, and TPS, can be used in the immunization and immunotherapy process of the invention. In either case $^3$H-TPS can be administered orally or parenterally.

Ordinarily the total quantity of $^3$H-TPS administered alone or jointly with tumor tissue DNA or TPS to provide immunity or an effective protective level against tumor development in a subject varies somewhat from species to species of mammal or fowl. Generally, it is desirable that the total quantity or overall dose of $^3$H-TPS alone or with the DNA, or TPS, or both, be administered in divided doses, i.e., TPS and DNA given as separate injections, or TPS alone, given singly on separate days. For example, doses may be given on from about 3 successive days to about 6 to 8 successive days, and thereafter at weekly intervals for from about 7 to about 17 weeks, resulting in a total of from about 10 to about 25 separate doses. However, it is advantageous to administer single doses to newborn animals especially in the early days of life.

The individual doses for immunization can vary. For example, for $^3$H-TPS alone can vary from about 0.25 μg to about 25 μg (e.g. of dried, such as lyophilized), specific activity about 75 mc/mg (i.e., millicuries per milligram) end product of the procedure of Section A, above. Then the total of the doses for an overall treatment can vary from about 3 to about 500 μg for $^3$H-TPS.

When tumor tissue DNA is administered in immunotherapy, i.e. in treatment after tumor development, the individual dose of tritiated TPS can vary from about 0.05 to about 100 μg and the DNA single dose can vary from about 0.2 to about 100 μg. Then the total quantity of all of the doses of the TPS can vary from about 0.8 μg to about 1000 μg, and that of the DNA from about 4 to about 1000 μg. They can be administered jointly (but separately) on successive days for from about 3 to about 8 days or every other day for a total of possibly 9 doses, and then followed by once weekly for from about 12 to about 23 weeks, for an overall total of from about 20 to about 29 doses.

F. TPS-DIAL-LPS

The TPS in TPS-dial -LPS, is linked to the lipopolysaccharide (LPS) through an invening lower aliphatic dialdehyde moiety (namely, succindialdehyde, glutaraldehyde, formaldehyde, malonic aldehyde or glyoxal). The LPS is obtained by the method provided by George B. Selzer (Bulletin of the Parenteral Drug Association, May-June 1970, volume 24 No. 3, pages 153-156, from p. 154 last paragraph through p. 155 column 2 middle paragraph), from a pathogenic or pyrogenic bacterium, for example, *E. coli, Alcal, fecalis,* Flavobacter, *E. Cloacae,* Pseudomonas, Herrellea, Kebsiella, *S. marcescens, F. aeroginosa, E. aerogenes, E. Liquif,* and *Propioni Bacterium* (acne), or a mycobacterium, a staphlococcus or streptococcus.

This so modified TPS, briefly called TPS-dial-LPS, more specifically is a polysaccharide-like antigenic substance of glycoprotein character conjugated with glyoxal, propandial, glutaraldehyde, or succindialdehyde, in turn conjugated with a lipopolysaccharide of pathogenic or pyrogenic bacterial source.

Preparation of TPS-dial-LPS is illustrated by, but is not to be restricted to, the following example wherein the TPS used for illustration was obtained from human lung carcinoma tissue by the method described in Section A, above.

EXAMPLE 2

TPS-dial-LPS was prepared by:

(a) adequately mixing at between ambient temperature and 5° C. (i) an aqueous solution of TPS (substantially free of unbound protein) of a suitable dilution containing about 0.027 gamma of TPS per ml. in the ratio of about 9 ml. (ii) to 1 ml. of an about 0.0025% aqueous solution of the selected lower aliphatic dialdehyde, glutaraldehyde, and allowing the resulting mixed solution to stand for a sufficient time (e.g. about 10 to 30 minutes or so) for the TPS and lower aliphatic dialdehyde to become conjugated thereby providing what briefly can be designated the "TPS-dial" (or on using glutaraldehyde, the "TPS-G") conjugate;

(b) similarly mixing about 9 ml. of an aqueous solution containing about 0.2 gamma of LPS (for example, of Klebsiella, No. 12833 American Type Culture Collection, Rockville, Md.) with 1 ml. of the about 0.0025% solution of the aliphatic dialdehyde (e.g. glutaraldehyde) and also allowing the resulting mixed solution to stand similarly for the LPS and the dialdehyde to become conjugated and provide what can be called the "LPS-dial" (or on using glutaraldehyde, the "LPS-G") conjugate; and (c) then similarly mixing 9 volumes of the TPS-dial or TPS-G conjugate with from 1 to 9 volumes of the LPS-dial (or LPS-G) conjugate and allowing the resulting TPS-dial and LPS-dial (or TPS-G and LPS-G) mixture stand for these two initial conjugates to provide the final desired TPS-dial LPS (or TPS-G-LPS) double conjugate.

When equal volumes of the above TPS-dial and LPS-dial solutions are mixed to provide the corresponding final TPS-dial-LPS (double conjugate) solution, the latter will contain about 52.04 gamma per ml of the double conjugate (composed of about 0.24 gamma of the TPS moiety, 1.8 gamma of the LPS moeity, and 50 gamma of the dialdehyde moiety).

In the foregoing illustrative example of the preparation of a TPS-dial-LPS double conjugate, and specifically the TPS-G-LPS double conjugate, and in any of the following possible modifications of that example, the TPS from lung carcinoma tissue can be replaced in part or in whole by the TPS derived from any other mammal or fowl malignant tumor tissue as described earlier above in section A. So also, the glutaraldehyde used in that example and in any herein described possible modifications of it can be replaced in part or in whole by any of glyoxal, propandial or succindialdehyde. Then too, the LPS obtained from Klebsiella can be replaced in the fully described illustrative example as well as in any of the just described possible modifications of it to provide in each of all of these various possible modifications the corresponding TPS-dial-LPS double conjugate, just as if each such possible modification were presented respectively fully recited herein.

Alternatively, instead of preparing the LPS-dial conjugate, 9 parts of the TPS solution containing, for example, 0.027 gamma of TPS per ml. can be admixed with 2 parts of the aqueous 0.0025% solution of the dialdehyde and their mixture let stand a sufficient time for the TPS-dial to be formed and then admixed with 9 parts of the LPS solution containing, for example, 0.2 gamma of LPS per ml.

The concentrations of the respective component aqueous solutions may be varied, but it is advisable that the concentration of the dialdehyde solution not exceed 0.0025% as to glutaraldehyde. The LPS can vary from about 0.85 to about 7.5 parts, and the dialdehyde from about 115 to about 205 parts, per single part of the TPS, by weight.

So far as presently indicated, the best way to administer the TPS-dial-LPS is intradermally. Dosages for therapy can start, for example, with diluting the concentration of TPS-dial-LPS of the above example from between one part in a million or more to one in 100,000 parts of physiological saline solution and increasing the concentration in stages to from one part in 10,000 and to one in 1000. Such injections of 0.1 to 0.2 ml. each can be given initially preferably once every other day for 2 weeks, then once weekly for several weeks (say, possibly 3 to 5 weeks), and then once per month for 3 months. This regimen can be varied in accordance with the nature, location and stage of the tumor, and the individual subject's response.

While the immunization part of the method of the invention may be applied at any age of the living subjects, generally it is better to apply it to the young animal, for example, during the first week of life or even commencing with the first day, as in the case of those of relatively short life span such as mice or fowl to about quite soon after the first year of life in those of longer life span.

The invention may be illustrated by, but not restricted to, the following examples:

EXAMPLE 3

Immunization in mice by tritiated TPS

Each of 10 new-born AKR Swiss mice received daily subcutaneous injections of 0.83 $\mu g$ each of $^3H$-TPS-sarcoma 180 (containing 0.073 mc/mg) on the first, second and third days of life and thereafter 17 weekly intraperitoneal injections of the same concentration starting on the 7th day of life and ending on the 132nd day, for a total of about 17 $\mu g$ for the 20 injections.

Three days after the final injection, i.e. on the 135th day of age, there was transplanted by the trocar method into the right axillary region of each of these 10 mice approximately 2 $mm^3$ (i.e. cubic millimeters) of mouse sarcoma 180 obtained from donor mice. The donor mice were obtained from the Jackson Laboratories in Bar Harbor, Ma., and kept in applicant's laboratories for a week and then used for the transplantation on the 11th day of the tumor age.

The tumor was removed under sterile conditions into a sterile Petri dish and minced with sterile scissors. The test mice were observed daily starting with the 5th day after the tumor transplant. Tumor measurements were noted every other day in terms of mean diameter growth (MDG) as the mean of its longest diameter in millimeters and that of another such diameter at right angles to the longest. To be considered a tumor take, the transplanted tumor should have an MDG of 6 mm or more.

Five days after tumor implant, four of the 10 test mice showed a tumor take, at the end of the 10th day six of the 10 showed a tumor take and at the end of the 14th day, only five of the 10 mice showed a tumor take. By the 83rd or 84th day after the tumor implant, all 10 test mice were living. They were then sacrificed and 7 of the 10 showed immunological protection evidenced by lack of significant tumor growth. To be considered as a cure it was necessary that a regression of the tumor be obtained from an MDG of 6 mm or more to an MDG of less than 6 mm.

Report No. 3-55 (1955) of the National Advisory Cancer Council, page 5 etc. states that mouse sarcoma 180 has (i) nearly 100% transplantability with uniform growth, (ii) low regression rate, (iii) no required mouse strain, and (iv) intermediate sensitivity to adverse agents. It continues that this tumor normally will "take" in 95 to 100% of the implants made and will grow with considerable uniformity. In addition the low baseline of natural regressions and the right degree of sensitivity all help to make less uncertain the interpretation of results in which the tumors fail to grow or grow poorly as a possible result of treatment.

EXAMPLE 4

Immunization in mice by ordinary TPS and DNA, and Immuno-therapy with 3H-TPS Each of 10 new-born AKR Swiss mice received daily intraperitoneal injections of 100 $\mu g$ each of TPS-sarcoma 180 on each of the first through ninth day of life for a total of 900 $\mu g$ per mouse. Between the 10th and 30th days, each of them received subcutaneously every other day 100 $\mu g$ of mouse DNA-sarcoma 180, for a total of 1000 $\mu g$ per mouse. Then every third day between the 39th and 80th day of age, each of them received subcutaneously 100 $\mu g$ of the TPS on the left side and 100 $\mu g$ of that DNA on the right side, for a total of 1300 $\mu g$ each of the TPS and of the DNA.

On the 5th day after tumor implant, 6 of these test mice showed a tumor take and at the end of the 10th and 15th days each of the 10 mice showed a tumor take and an average MDG of 10.9 mm and 13.4 mm respectively.

On the 15th day after tumor transplant each of these 10 mice was given one treatment (intravenously to each male, and orally to each female) of 0.3 ml. per 30 gram mouse of $^3H$-TPS-sarcoma 180 with activity of 200 uc/ml and concentration of 2.72 mg. per ml.

On the 83rd and 84th day all 10 test mice were still alive. They were then sacrificed and 9 of the 10 showed a cure, i.e. the tumor MDG was less than 6.0 mm.

The immuno-therapy in animals includes a preparative stage to induce specific antigenic receptivity of the reticuloendothelial system by administering $^3H$-TPS jointly with tumor-derived DNA, about in the dosages and regimen described earlier above.

That was followed by a complementary treatment involving intraveneous, or better, oral administration of tritiated-TPS, for example, at a dosage of 0.3 ml. per 30 gm. mouse (containing 0.83 $\mu g$ of tritiated-TPS with an activity of 60 uc.), as on the 15th day of the tumor age (in the case of implanted tumor).

EXAMPLE 5

$^3H$-TPS by contact and TPS by injection

A group of 9 new-born AKR Swiss mice on the third day of life were placed in the same cage with a second group of 7 such mice who were receiving parenteral injections of $^3H$-TPS-sarcoma 180 and nursed with them from the same mother for a period of three weeks. Each of the first group of 7 mice which were not given $^3H$-TPS received instead a total of 12 injections of 0.25 $\mu g$ each of TPS-sarcoma 180 daily subcutaneously for the first three days of life followed by intraperitoneal injections on the 6th and 7th days and once weekly thereafter for the remaining seven doses. After that period they were weaned and placed in a separate cage on the same table with the others.

On the 70th day of life, sarcoma 180 from the same source and in the same manner as in Example 1 was transplanted into each of these first seven mice, and they were sacrificed about 40 days later. The cures amounted to 29% with a death rate of only 14%.

EXAMPLE 6

Contact with 3H-TPS

A first group of 7 new-born AKR Swiss mice was placed in a cage with a second such group treated as in Example 5 with the $^3$H-TPS, but without giving the first group any injections or other direct treatment. These latter otherwise were handled as in that Example, and at the end showed 71% cures and no deaths. Liquid scintillation examination of lymph nodes, initial tumor sites, and other body organs of these mice showed radioactivity levels which could have resulted only from contact with $^3$H-TPS from their thus treated suckling cage mates.

G. Immuno-Therapy in Mice Against Subcutaneously Implanted Sarcoma 180

A controlled study was conducted to determine which combination of agents, dosage rates and regimens, provided the most effective prolongation of life in mice implanted with Sarcoma 180 tumor, known to be associated with an extremely high mortality rate. See discussion above at p. 19 lines 4–14.

EXAMPLE 7

Tumor implantation

A group of 40 random bred Swiss (CD) female mice (obtained from Charles River Laboratories) were each inoculated subcutaneously with 0.1 ml of Crocker Sarcoma 180 tumor homogenate.

TABLE I
GROWTH INHIBITION OF SUBCUTANEOUSLY IMPLANTED SARCOMA 180 WITH SELECTED MATERIALS

| GROUP | TEST MATERIAL | DOSE mg/inj | ROUTE | Δ (g) 8 | Δ (g) 15 | DAY 8 Mean Volume | DAY 8 T/C | DAY 15 Mean Volume | DAY 15 T/C | DAY 22 Mean Volume | DAY 22 T/C | DAY 22 Median Volume | DAY 22 T/C |
|---|---|---|---|---|---|---|---|---|---|---|---|---|---|
| 1 | UNTREATED CONTROLS | | | +0.8 | +3.8 | 175 +/− 99 | 222 | 214 +/− 119 | 246 | 157 +/− 115 | 222 | 122 | 144 |
| | | | | +0.8 | +4.8 | 175 +/− 60 | +/− | 293 +/− 129 | +/− | 271 +/− 290 | +/− | 149 | |
| | | | | +1.4 | +4.7 | 175 +/− 43 | 117 | 181 +/− 85 | 127 | 123 +/− 127 | 294 | 82 | |
| | | | | +1.5 | +4.0 | 360 +/− 125 | | 297 +/− 143 | | 335 +/− 479 | | 196 | |
| 2 | 0.9% NaCl | 0 | ip | +1.5 | +5.0 | 345 +/− 301 | 1.55 | 176 +/− 58 | 0.72 | 218 +/− 288 | 1.30 | 126 | 0.88 |
| 3 | 3H-TPS | 3 | ip | −0.6 | +2.6 | 199 +/− 88 | 0.90 | 253 +/− 161 | 1.03 | 556 +/− 541 | 2.50 | 304 | 2.11 |
| 4 | | 9 | | −0.8 | +3.3 | 209 +/− 66 | 0.94 | 195 +/− 91 | 0.79 | 261 +/− 196 | 1.18 | 209 | 1.45 |
| 5 | | 30 | | −0.6 | +2.0 | 238 +/− 62 | 1.07 | 239 +/− 138 | 0.97 | 373 +/− 629 | 1.68 | 144 | 1.00 |
| 6 | TPS | 3 | ip | +1.1 | +3.7 | 191 +/− 55 | 0.86 | 138 +/− 43 | 0.56 | 129 +/− 115 | 0.58 | 88 | 0.61 |
| 7 | | 9 | | +0.6 | +3.5 | 211 +/− 159 | 0.95 | 97 +/− 76 | 0.39 | 57 +/− 50* | 0.26 | 36 | 0.25 |
| 8 | | 30 | | +1.3 | +4.3 | 236 +/− 138 | 1.06 | 162 +/− 88 | 0.66 | 70 +/− 91* | 0.32 | 32 | 0.22 |
| 9 | DNA | 3 | ip | +1.0 | +2.8 | 196 +/− 112 | 0.83 | 207 +/− 161 | 0.84 | 327 +/− 372 | 1.47 | 196 | 1.36 |
| 10 | | 9 | | +1.3 | +4.2 | 249 +/− 126 | 1.12 | 199 +/− 188 | 0.77 | 195 +/− 327 | 0.88 | 63 | 0.44 |
| 11 | | 30 | | +1.5 | +4.8 | 198 +/− 110 | 0.89 | 179 +/− 111 | 0.73 | 184 +/− 279 | 0.83 | 96 | 0.67 |
| 12 | 0.9% NaCl | 0 | po | +1.0 | +3.8 | 238 +/− 82 | 1.07 | 224 +/− 71 | 0.91 | 208 +/− 145 | 0.94 | 197 | 1.37 |
| 13 | 3H-TPS | 3 | po | +0.2 | +3.3 | 239 +/− 111 | 1.30 | 226 +/− 91 | 1.00 | 223 +/− 178 | 1.00 | 158 | 1.10 |
| 14 | | 9 | | −0.4 | +0.5 | 209 +/− 97 | 0.94 | 177 +/− 80 | 0.92 | 104 +/− 51 | 0.47 | 94 | 0.65 |
| 15 | | 30 | | −0.4 | +2.9 | 210 +/− 81 | 0.95 | 278 +/− 158 | 1.13 | 312 +/− 302 | 1.41 | 184 | 1.28 |
| 16 | TPS | 3 | po | +1.1 | +2.9 | 251 +/− 126 | 1.13 | 223 +/− 111 | 0.91 | 138 +/− 104 | 0.62 | 108 | 0.75 |
| 17 | | 9 | | +1.4 | +3.4 | 171 +/− 79 | 0.77 | 168 +/− 75 | 0.68 | 136 +/− 93 | 0.61 | 108 | 0.75 |
| 18 | | 30 | | +1.2 | +4.4 | 263 +/− 114 | 1.18 | 330 +/− 133 | 1.34 | 665 +/− 970 | 3.00 | 327 | 2.27 |
| 19 | 0.9% NaCl + Adj | 0 | im | +1.5 | +4.0 | 252 +/− 87 | 1.14 | 137 +/− 56 | 0.56 | 104 +/− 56 | 0.47 | 88 | 0.61 |
| 20 | TPS | 9 | im | +0.7 | +4.1 | 214 +/− 74 | 0.96 | 222 +/− 113 | 0.50 | 329 +/− 333 | 1.48 | 197 | 1.37 |
| 21 | | 30 | | +1.6 | +4.6 | 220 +/− 102 | 0.99 | 197 +/− 150 | 0.80 | 132 +/− 80 | 0.59 | 172 | 1.19 |
| 22 | DNA | 9 | im | +1.4 | +4.5 | 235 +/− 75 | 1.06 | 138 +/− 115 | 0.56 | 107 +/− 60 | 0.48 | 82 | 0.57 |
| 23 | | 30 | | +2.1 | +5.2 | 267 +/− 141 | 1.20 | 171 +/− 131 | 0.70 | 98 +/− 69 | 0.44 | 88 | 0.61 |
| 24 | Cyclophosphamide (mg/kg) | 20 | ip | +1.1 | +2.6 | 179 +/− 136 | 0.81 | 176 +/− 102 | 0.72 | 386 +/− 325 | 1.74 | 172 | 1.19 |
| 25 | | 40 | | +1.1 | −0.1 | 151 +/− 117 | 0.68 | 266 +/− 185 | 1.08 | 710 +/− 398** | 3.20 | 707 | 4.91 |
| 26 | | 80 | | +0.4 | −1.2 | 121 +/− 70 | 0.55 | 59 +/− 42 | 0.24 | 47 +/− 30* | 0.21 | 50 | 0.35 |
| 27 | TPS/DNA | 9/9 | im/im | +1.8 | +5.7 | 331 +/− 233 | 1.49 | 200 +/− 113 | 0.81 | 320 +/− 412 | 1.44 | 239 | 1.65 |
| 28 | 3H-TPS/TPS/DNA | 30/30 | | +1.6 | +5.5 | 218 +/− 121 | 0.98 | 206 +/− 245 | 0.84 | 479 +/− 884 | 2.16 | 184 | 1.28 |
| 29 | | 9/9/9 | po/im/im | +0.4 | +3.9 | 242 +/− 104 | 1.09 | 204 +/− 86 | 0.83 | 205 +/− 151 | 0.92 | 144 | 1.00 |
| 30 | | 30/30/30 | po/im/im | +0.3 | +3.1 | 251 +/− 75 | 1.13 | 226 +/− 120 | 0.92 | 155 +/− 93 | 0.70 | 149 | 1.03 |

| GROUP | TEST MATERIAL | DOSE mg/inj | ROUTE | Δ (g) 8 | Δ (g) 15 | DAY 30 Mean Volume | DAY 30 T/C | DAY 30 Median Volume | DAY 30 T/C | DAY 35 Mean Volume | DAY 35 T/C | DAY 35 Median Volume | DAY 35 T/C |
|---|---|---|---|---|---|---|---|---|---|---|---|---|---|
| 1 | UNTREATED CONTROLS | | | +0.8 | +3.8 | 130 +/− 91 | 273 | 144 | 75 | 109 +/− 116 | 320 | 76 | 63 |
| | | | | +0.8 | +4.8 | 511 +/− 784 | +/− | 92 | | 962 +/− 1760 | +/− | 44 | |
| | | | | +1.4 | +4.7 | 71 +/− 83 | 635 | 36 | | 84 +/− 91 | 941 | 48 | |
| | | | | +1.5 | +4.0 | 379 +/− 985 | | 36 | | 103 +/− 78 | | 63 | |
| 2 | 0.9% NaCl | 0 | ip | +1.5 | +5.0 | 505 +/− 1409 | 1.85 | 52 | 0.69 | 729 +/− 2125 | 2.28 | 60 | 0.95 |
| 3 | 3H-TPS | 3 | ip | −0.6 | +2.6 | 884 +/− 1657 | 3.24 | 198 | 2.64 | 1201 +/− 2548 | 3.75 | 154 | 2.44 |
| 4 | | 9 | | −0.8 | +3.3 | 120 +/− 125 | 0.44 | 69 | 0.92 | 126 +/− 201 | 0.39 | 40 | 0.63 |
| 5 | | 30 | | −0.6 | +2.0 | 552 +/− 1201 | 2.02 | 75 | 1.00 | 1310 +/− 3128 | 4.12 | 75 | 1.19 |
| 6 | TPS | 3 | ip | +1.1 | +3.7 | 129 +/− 210 | 0.47 | 32 | 0.43 | 213 +/− 465 | 0.67 | 32 | 0.51 |
| 7 | | 9 | | +0.6 | +3.5 | 16 +/− 12 | 0.05 | 14 | 0.19 | 18 +/− 12 | 0.06 | 18 | 0.29 |

TABLE I-continued

GROWTH INHIBITION OF SUBCUTANEOUSLY IMPLANTED SARCOMA 180 WITH SELECTED MATERIALS

| # | Material | Dose | Route | | | | | | | | | |
|---|---|---|---|---|---|---|---|---|---|---|---|---|
| 8 | DNA | 30 | ip | +1.3 +4.3 | 162 +/− 353 | 0.59 | 49 | 0.53 | 315 +/− 851 | 1.05 | 63 | 1.00 |
| 9 | | 3 | | +1.0 +2.8 | 647 +/− 1440 | 2.37 | 75 | 1.00 | 1348 +/− 3141 | 4.21 | 69 | 1.10 |
| 10 | | 9 | | +1.3 +4.2 | 446 +/− 1170 | 1.88 | 32 | 0.43 | 575 +/− 1700 | 1.80 | 40 | 0.63 |
| 11 | | 30 | | +1.5 +4.8 | 367 +/− 954 | 1.84 | 66 | 0.88 | 655 +/− 1307 | 2.05 | 36 | 0.57 |
| 12 | 0.9% NaCl | 0 | po | +1.0 +3.8 | 124 +/− 137 | 0.45 | 82 | 1.09 | 129 +/− 167 | 0.38 | 69 | 1.10 |
| 13 | 3H-TPS | 3 | po | +0.2 +3.3 | 281 +/− 622 | 1.04 | 40 | 0.53 | 491 +/− 1172 | 1.53 | 38 | 0.57 |
| 14 | | 9 | | −0.4 +0.5 | 75 +/− 101 | 0.27 | 44 | 0.59 | 34 +/− 28 | 0.11 | 25 | 0.40 |
| 15 | | 30 | | −0.4 +2.9 | 395 +/− 823 | 1.45 | 86 | 1.15 | 697 +/− 1419 | 2.18 | 63 | 1.00 |
| 16 | TPS | 3 | po | +1.1 +2.9 | 115 +/− 91 | 0.42 | 75 | 1.00 | 57 +/− 36 | 0.18 | 48 | 0.76 |
| 17 | | 9 | | +1.4 +3.4 | 76 +/− 74 | 0.28 | 56 | 0.75 | 127 +/− 235 | 0.40 | 44 | 0.70 |
| 18 | | 30 | | +1.2 +4.4 | 1112 +/− 1819 | 4.07 | 198 | 2.64 | 2183 +/− 3448 | 6.82 | 176 | 2.79 |
| 19 | 0.9% NaCl + Adj | 0 | im | +1.5 +4.0 | 70 +/− 64 | 0.28 | 36 | 0.48 | 87 +/− 93 | 0.27 | 64 | 1.02 |
| 20 | TPS | 9 | im | +0.7 +4.1 | 193 +/− 254 | 0.71 | 82 | 1.09 | 140 +/− 239 | 0.44 | 40 | 0.63 |
| 21 | | 30 | | +1.6 +4.6 | 45 +/− 44 | 0.16 | 19 | 0.53 | 43 +/− 79 | 0.13 | 9 | 0.14 |
| 22 | DNA | 9 | im | +1.4 +4.5 | 64 +/− 35 | 0.23 | 58 | 0.77 | 57 +/− 70 | 0.18 | 32 | 0.51 |
| 23 | | 30 | | +2.1 +5.2 | 34 +/− 30 | 0.12 | 86 | 0.78 | 60 +/− 69 | 0.19 | 48 | 0.76 |
| 24 | Cyclophosphamide | 20 | ip | +1.1 +2.6 | 2601 +/− 1177** | 9.58 | 365 | 4.87 | 1658 +/− 1968 | 5.17 | 726 | 11.52 |
| 25 | (mg/kg) | 40 | | +1.1 −0.1 | 2446 +/− 1187** | 8.96 | 2674 | 35.65 | 2854 +/− 1004** | 8.92 | 3220 | 51.11 |
| 26 | | 80 | | +0.4 −1.2 | 478 +/− 302 | 1.75 | 488 | 6.18 | 1142 +/− 426** | 3.57 | 1008 | 16.00 |
| 27 | TPS/DNA | 9/9 | im/im | +1.8 +5.7 | 703 +/− 1237 | 2.58 | 152 | 2.83 | 1319 +/− 2417 | 4.12 | 82 | 1.30 |
| 28 | | 30/30 | | +1.6 +5.5 | 1220 +/− 2661 | 4.47 | 75 | 1.00 | 1724 +/− 3707 | 5.39 | 74 | 1.17 |
| 29 | 3H-TPS/TPS/DNA | 9/9/9 | po/im/im | +0.4 +3.9 | 275 +/− 340 | 1.01 | 182 | 2.16 | 477 +/− 614 | 1.49 | 196 | 3.11 |
| 30 | | 30/30/30 | po/im/im | +0.3 +3.1 | 62 +/− 42 | 0.23 | 80 | 0.89 | 41 +/− 37 | 0.13 | 32 | 0.52 |

*Significantly smaller than untreated controls at p < .01 by student's test.
**Significantly larger than untreated controls at p < .01 by student's test.

The tumor material was taken from 7-8 day old solid subcutaneous tumor, debrided of necrotic material, and homogenized in a Potter-Elvehjem pestle homogenizer.

The mice were weighed on days 1, 8, 15 for evidence of toxicity. Tumors were measured in perpendicular diameters with vernier calipers on days 8, 15 and 35, and tumor volume calculated by treating the tumor as an ellipsoid. The growth of the tumors in the untreated controls is tabulated in Table 1.

EXAMPLE 8

Saline Injection 10 mice inoculated with tumor sarcoma 180 as in Example 7 were injected with physiological saline as a control. Injections of 0.3 ml were administered intraperitoneally (ip) daily on days 5-13 (day 0=tumor implant). The results for this group are shown in Table 1. As an indication of the effectiveness of a given treatment the T/C (treated animal tumor mean volume to control animal mean volume) ratio is calculated, i.e., a ratio less than 1.00 indicates a reduction in mean tumor volume compared to the control tumor. The treated actual tumor median volume versus control median volume is also shown.

EXAMPLE 9

$^3$H-TPS Injection 3 groups of 10 mice each inoculated as in Example 7 were injected ip with $^3$H-TPS prepared as described in Section C, above. The three groups were given daily injections from day 5-13, post implant. The first group received a dose of 3 mg/mouse/injection, the second 9 mg/mouse/injection, and the third 30 mg/mouse/injection. The results are shown in Table 1 and indicate that the dosage of 9 mg/mouse/injection was effective in reducing tumor volume.

EXAMPLE 10

TPS Injection 3 groups of 10 mice each were treated as in Example 9 except that non-tritiated TPS was injected rather than $^3$H-TPS. The results shown in Table 1 reveal that the low dose (3 mg/mouse/injection) was more effective in reducing tumor volume, than the other two doses.

EXAMPLE 11

DNA Injection 3 groups of 10 mice each were treated according to Example 10, except that DNA prepared as described in Section D, above, was injected rather than TPS. The results are shown in Table 1.

EXAMPLE 12

Oral Saline 1 group of 10 mice was treated as in Example 8 except that the saline was administered orally (po) rather than ip. The results are shown in Table 1.

EXAMPLE 13

Oral $^3$H-TPS 3 groups of 10 mice each were treated according to Example 9 except that the H-TPS was administered po rather than ip. Again, the results in Table 1 indicate that the middle dose of 9 mg/mouse/administration was effective in reducing tumor volume.

EXAMPLE 14

Oral TPS 3 groups of 10 mice each were treated according to Example 13 except that TPS was administered rather than $^3$H-TPS. As in Example 10 the low dose (3 mg/mouse/administration) was more effective than the middle or high doses.

EXAMPLE 15

Saline Intramuscularly (im)

1 group of 10 mice was treated with a saline control. The saline was administered intramuscularly (im) and was given with complete Freund's adjunct on day 1 and with incomplete Freund's adjuvant on days 4 and 7 (post implant). The results are shown in Table 1.

EXAMPLE 16

TPS (im)

2 groups of 10 mice each were treated according to Example 15, except that TPS was injected rather than saline, at dosages of 9 and 30 mg/mouse/injection. The results in Table 1 show that the higher dosage was effective in reducing the T/C ratio.

EXAMPLE 17

DNA (im)

2 groups of 10 mice each were treated according to Example 10 except that DNA was administered rather than TPS. Table 1 reveals that both dosages were effective in reducing tumor volume.

EXAMPLE 18

Cyclophosphamide Injection 3 groups of 10 mice each were used as a treatment control. The reference compound cyclophosphamide was prepared daily in saline and injected ip at dosages of 80, 40 and 20 mg/kg/injection (milligrams per kilogram body weight per injection) daily from day 5-13. Table 1 shows that cyclophosphamide treatment was ineffective and resulted in very large T/C ratios.

EXAMPLE 19

TPS and DNA Injection 1 group of 10 mice was treated with a combination of TPS and DNA. Doses of 9 mg/mouse/injection of both TPS and DNA were administered im to the right leg and left leg respectively, on days 1, 4 and 7 (post implant). Table 1 shows that this regimen was ineffective in reducing the T/C ratio.

EXAMPLE 20

TPS and DNA Injection

The experiment of Example 19 was conducted and the dosage increased from 9 to 30 mg/mouse/injection. The higher dose was ineffective, as shown in Table 1.

EXAMPLE 21

$^3$H-TPS, TPS and DNA Administration 1 group of 10 mice was treated with a combination of three treatments. 9 mg/mouse/administration of $^3$H-TPS was administered po daily from day 5-13 post implant. The same dose of TPS and DNA was administered im in opposite legs on days 1, 4 & 7 post implant.

The addition of ³H-TPS to the treatment of Example 19 improved the response as shown in Table 1.

EXAMPLE 22

³H-TPS, TPS and DNA Administration

The experiment of Example 21 was conducted increasing the dosage to 30 mg/mouse/administration. The increased dose was even more effective in reducing the T/C ratio than the treatment of Example 21.

The results of Examples 6–22 show that there is some effectiveness in using the treatment of the present invention compared to the standard treatment (cyclophosphamide). In the case of sarcoma 180, a cancer which is known to ultimately cause 100% mortality, and where standard treatment is ineffective, any prolongation of life, and reduction in tumor volume is desirable.

The immunization method of the invention, illustrated in the preceding examples as applied to mammals, is similarly applicable to fowl. Fowl is used herein in its generic sense as including poultry and other fowl. The TPS for use with fowl can be derived from malignant tumor tissue, such as from the visceral organs of leucotic chickens, perhaps better from their livers or even from their gonads, as well as from tissue cultures such as one infected by the well known GA strain of fowl leucosis virus, by a process like that described in Section A or B above.

From this TPS (from leucosis tissue) there also can be prepared ³H-TPS by the Wilzbach process referred to in Section C above.

The TPS obtained from either leucotic tissues or a tissue culture infected with leucosis virus also can be conjugated with an aliphatic dialdehyde such as glutaraldehyde, and the resulting conjugate can be conjugated further with LPS obtained from a pathogenic or pyrogenic bacterial source such as Klebsiella to form the corresponding double conjugate as described earlier above in Section F.

Each of the antigenic agents as obtained from malignant tissue of leucotic chickens can be administered to the young chicks of a leucosis-susceptible strain (e.g., paralytic, optic or leucemic), beneficially starting with day old chicks, in immuno-prophylactic dosages as within the ranges disclosed earlier above administered by adding the dosage to their drinking water.

In many instances with such chicks, the immunization regimen can be relatively shorter, possibly as short as from 3 to 10 days, or 2 or 3 weeks or so. This regimen also can involve one exposure, as in the initial first few days of life, to ³H-TPS-containing water derived, for example, from the sources described in the third immediately preceding paragraph. The regimen can involve also one or two exposures, one on the first day of life and the second a week later, to drinking water containing a TPS-dial-LPS such as TPS-G-LPS.

H. Immunotherapy in Man

EXAMPLE 23

Melanoma

A white 60 year old male with a history of a malignant melanoma which was surgically removed on May 21, 1965 had a recurrence in the axillary nodes discovered early in October (4½ months later) which was removed by radical operation on October 17th. However, the wound had not healed by Dec. 31, 1965 when the patient then was given immunoprophylactic treatment with TPS obtained from melanoma and carcinoma tissues from other humans (from applicant's laboratory tissue bank) and prepared as described above in Section A.

1 ml. of a TPS solution containing 80 μg/ml of TPS prepared from human melanoma and carcinoma tissue (admixed with 1 ml. of 'Arlacel' fatty acid partial esters of a polyol as a hexitol as a nonionic emulsifier) was injected deep subcutaneously into the left arm. Simultaneously 1 ml. of DNA prepared as described above from similar tumor tissues (and also admixed with 1 ml. of the 'Arlacel' emulsifier) was injected also deep subcutaneously into the right arm. Those injections were repeated 2 days later and thereafter at irregular intervals until March, 1970. Starting with the first day of these injections, the patient took orally three times daily for 60 days about 0.5 mg. of tritiated-TPS specific acting 0.29 mc/mg (obtained from multi-source human carcinoma tissue). At the end of January 1966 (about three weeks after starting this treatment) the wound healed completely. These injections (instituted December 31, 1965) were repeated on January 28th, on March 1st, April 13, 1966 and Jan. 3, 1967.

This patient then was followed up by being given on Dec. 15, 1966 the complete tumor detection skin test described in my copending application Ser. No. 370,517, filed Apr. 21, 1982 to determine whether there might be an early recurrence of the melanoma. The test result was positive thereby indicating an early recurrence of the tumor.

Therefore, the patient then was given immunotherapy employing only the same set of injections of the TPS (i.e. omitting the oral tritiated material) admixed with the 'Arlacel' emulsifier as he was given before (i.e. starting Dec. 31, 1965). That treatment was repeated on Jan. 3, 1967. The tumor skin test was repeated on Feb. 21, 1967 and this time a negative result (i.e. showing no evidence of any tumor) was found. The subject was re-examined with the tumor skin test on Sept. 21, 1967 and on Jan. 20, 1968 and on each occasion showed a negative result. At a physical check-up about the beginning of 1970, he was found to be in complete good health, and declared to be a "five-year cure". In February, 1981, the patient reported that he is still in good health.

EXAMPLE 24

Human Fibrosarcoma

A 38 year old white male with a history of recurrent fibrosarcoma since 1962, the first recurrence having been in January 1963, the second in August 1963, the third in March, 1964, the fourth in March 1965 and the fifth in November, 1965, was given immuno-prophylactic treatment starting on Jan. 20, 1966. That day he received a subcutaneous injection of TPS prepared as described above from multi-source human sarcoma and carcinoma tissues, and another of DNA derived as also above-described from like tissues. He also took orally, three times daily, ³H-TPS from like tissues until surgery a week later, but discontinued it after a few days having then used only 15 ml. of the ³H-TPS, or a total of only 7.5 microcuries, of the amount of ³H-TPS given to him to use for treatment.

Wound healing progressed very satisfactorily and he was free of tumor recurrence for thirteen months. On Mar. 7, 1967, he consulted his surgeon who found on X-ray a small metastatic focus in the lung. In July of 1967, this patient was given yttrium microspheres intravenously, but died on Aug. 8, 1967. His death occurred a year and a half after the treatment which he had taken (although incompletely) according to this invention, for his dermato-fibrosarcoma, and leads to the belief that this treatment may have helped in delaying the recurrence of his tumor disease.

I. Immunotherapy Regimens

Immuno-therapy in man can also include a preparative stage to induce specific antigenic receptivity of the tumorous patient's reticuloendothelial system. For that there usually is used separate parenteral solutions of the 'Arlacel' emulsifier and physiological saline (i) one with 5 mg of TPS (preferably from tissue of the same type of malignant tumor taken from another person, as from a tissue bank), and (ii) the other with 10 mg of tumor-derived DNA (also from a similar source).

On the first and third days, 2 ml. of a TPS solution containing 180–250 µg/ml are injected subcutaneously in, e.g. the patient's left arm; and similarly 2 ml. of the DNA solution containing 100 µg/ml are injected on the same day into the other arm. Then both injections are repeated at intervals of 7 to 10 days for a total of 3 or more such dual injections, and followed by from about 5 to about 15 more such injections at intervals of about 10 to about 21 days each as indicated by the patient's clinical response (e.g. gaining of weight, voice strengthening) such as forming of a strong positive skin reaction (i.e. erythema) to intradermal injection of the same TPS.

A simultaneous complementary treatment involving administration of $^3$H-TPS given either parenterally and/or orally is also used. In the unusual event of an unforseen complication deleterious to the patient, simultaneous parenteral administration of the tritiated-TPS may be given with the oral until adequate improvement occurs.

Oral administration of $^3$H-TPS, so far as presently indicated, is desirable three times daily at 30 minutes before meals, at an ascending regimen starting with a minimum initiating dose of 0.5 microcuries for 1.5 microcuries per day given for each of the first 3 days, none on the 4th, continued on the 5th to 7th, none on the 8th, and repeated on the 9th to 11th, and none on the 12th.

The dose then is increased to 0.88 microcuries given 3 times daily (a total of 2.64 microcuries daily) on the 13th to 15th, 17th to 19th, and 21st to 23rd days, with none on the 16th, 20th and 24th days.

Then the dose is raised to 1.1 microcuries 3 times daily (total of 3.3 daily) for the 25th to 27th, 29th, 30th, 33rd to 35th and 43rd to 46th days, with none on the 28th, 31st, 32nd, and 36th through 42nd days.

Dosage then is increased to 1.5 microcuries each 3 times daily (total of 4.5 per day) given on the 47th, 54th through 59th, 61st to 63rd, 72nd through 78th, 87th through 91st, 100th through 103rd, and 112th through 116th days, with none on the 48th through 53rd, 60th, 64th through 71st, 79th through 86th, 92nd through 99th, and 104th through 111th days.

The foregoing typical regimen can be varied up or down as governed by the patient's progress. The parenteral dose varies from 0.25 to 1 microcurie in a single daily dose (e.g. with calcium gluconate or other suitable intravenous vehicle) every other day for a total of 2 to 3 doses. However, so far as presently indicated, the oral treatment appears to be more desirable and the parenteral can be combined with it. Intravenous injection should be used only with advanced tumor cases where serious complications and intractable pain indicate need for immediate high level intervention.

The following examples illustrate this treatment:

EXAMPLE 25

Cancer of Pancreas

A 43 year old while male showing marked loss (40 lbs.) of weight and jaundice was started on immunotherapy treatment on May 10, 1963, and early in the following week was operated on. Cancer of the head of the pancreas was found but removal was determined to be inadvisable. The patient was then continued on an oral tritiated-TPS regimen together with intravenous injections of 0.5 mc. (i.e. millicurie) each.

| Date | Treatment | Aministration Route |
|---|---|---|
| 5/10/63 | $^3$H-TPS 0.55 mc | oral |
|  | TPS and DNA 200 ug each | IV |
| 5/11 | $^3$H-TPS 0.55 mc | oral |
| 5/12 | $^3$H-TPS 0.55 mc | oral |
|  | TPS and DNA, 200 ug each | IV |
| 5/14 | $^3$H-TPS 0.55 mc | oral |
| 5/18 | $^3$H-TPS 0.38 mc | IV |
|  | TPS and DNA, 200 ug each | IV |
| 5/23 | $^3$H-TPS 0.55 mc | oral |
|  | TPS and DNA, 200 ug each | IV |
| 5/24 | $^3$H-TPS 0.55 mc | oral |
| 5/30 | $^3$H-TPS 0.55 mc | oral |
| 6/25 | $^3$H-TPS 0.27 mc | oral |

The patient's health thereafter improved, he regained his weight, and resumed his employment. When last examined on Nov. 16, 1965, he gave no evidence of cancer. When contacted on Mar. 18, 1970, the patient was still alive and well; his only problem, seven years after being cured following this therapy, is that he is rather overweight for his height. The patient was still alive and well when last contacted by the applicant in 1981.

EXAMPLE 26

Mesothelioma

Operation on a 40 year old white male with marked swelling of the abdomen showed mesothelioma with metastatic nodules in the mesentery. Other than biopsy none of the tumor was removed. Instead, an oral and IV regimen with $^3$H-TPS and TPS and DNA was started on May 2, 1963 and continued for the full period after the patient's discharge from the hospital. The patient subsequently was able to return to work. However, the patient died on Mar. 13, 1965 after this prolonged survival quite unusual for this type of cancer.

| Date | Treatment | Administration Route |
|---|---|---|
| 5/2/63 | TPS and DNA, 200 mg each | IV |
|  | $^3$H-TPS 0.5 mc | Oral |
| 5/3 | TPS and DNA, 200 mg each | IV |
|  | $^3$H-TPS 0.5 mc | Oral |
| 5/4 | TPS and DNA, 200 mg each |  |
|  | $^3$H-TPS 0.5 mc |  |
| 5/6 | TPS and DNA, 200 mg each | IV |
|  | $^3$H-TPS 0.5 mc | Oral |
| 5/7 | TPS and DNA, 200 mg each | IV |
|  | $^3$H-TPS 0.5 mc | Oral |
| 5/10 | TPS and DNA, 200 mg each |  |
|  | $^3$H-TPS 0.5 mc |  |
| 5/14 | TPS and DNA, 200 mg each | IV |
|  | $^3$H-TPS 0.5 mc | Oral |
| 5/18 | TPS and DNA, 200 mg each | IV |
|  | $^3$H-TPS 0.5 mc | Oral |

-continued

| Date | Treatment | Administration Route |
|---|---|---|
| 5/25 | TPS and DNA, 200 mg each | |
| | ³H-TPS 0.5 mc | |
| 6/7 | ³H-TPS 0.11 mc | Oral |
| | TPS and DNA, 200 mg each | IV |
| 8/6 | TPS and DNA, 200 mg each | |
| 8/15 | ³H-TPS 0.07 mc | Oral |

EXAMPLE 27

Metastatic papillary adenocarcinoma

A 45 year old white married female was diagnosed as operation as having metastatic papillary adenocarcinoma involving both ovaries and the entire peritoneal cavity with metastatic lesions in the pleura. Only one ovary was removed. The patient was considered to be terminal and was suffering from repeated accumulation of fluid in the pleura from metastatic lesions. Treatment with ³H-TPS orally (0.029 mc/mg) and with large parenteral doses was started on Jan. 17, 1963 shortly before operation (which the patient withstood very well), and continued orally from the full course thereafter.

| Date | Treatment | Administration Route |
|---|---|---|
| 1/17/63 | ³H-TPS 1 mc | IV |
| 1/19 | ³H-TPS 1 mc | IV |
| 1/20 | ³H-TPS 0.5 mc | Left pleural infusion |
| 1/28 | ³H-TPS 1.0 mc | oral |
| 2/6 | ³H-TPS 1.0 mc | oral |
| 4/23 | ³H-TPS 0.5 mc | Right pleural infusion |

The patient fared unexpectedly well post-operation for three months when she resumed her normal activities. Shortly thereafter she developed pneumonia and died on Apr. 8, 1963. Autopsy findings evidenced that the tumor lesions were smaller in size than at operation.

EXAMPLE 28

Multiple myeloma

A 50 year old male with extremely severe sciatic pain in the back and legs showed definite diagnosis of multiple myeloma on biopsy. Other than for biopsy, no tissue was removed. On May 27, 1963 the oral administration of tritiated-TPS (0.029 mc/mg) was started together with parenteral doses.

| Date | Treatment | Administration Route |
|---|---|---|
| 5/27/63 | TPS, 36 ug and DNA, 100 ug | IV |
| | ³H-TPS 0.5 mc | IV |
| 5/28 | ³H-TPS 0.5 mc | IV |
| 5/29 | ³H-TPS 0.5 mc | oral |
| 5/30 | ³H-TPS 0.5 mc | oral |
| 5/31 | TPS, 36 ug and DNA, 100 ug | IV |
| | ³H-TPS 0.5 mc | IV |
| 6/1 | ³H-TPS 0.5 mc | oral |
| 6/3 | ³H-TPS 0.5 mc | oral |
| 6/13 | ³H-TPS 0.5 mc | IV |
| | TPS, 36 ug and DNA, 100 ug | IV |
| 6/17 | ³H-TPS 0.5 mc | oral |

Following such treatment the patient showed dramatic response with no more pain within 12 hours and resumed walking. On Dec. 13, 1963 the patient died of penumonia of the right lung.

EXAMPLE 29

Metastatic breast carcinoma

A 50 year old white female with history of metastatic carcinoma of the breast and bone metastasis with uncontrollable pain was started on the oral treatment on Apr. 26, 1963 with accompanying parenteral doses of ³H-TPS, resulting in dramatic loss of back and leg pains with X-ray evidence of improvement of the site of the bone destruction.

| Date | Treatment | Administration Route |
|---|---|---|
| 4/26/63 | ³H-TPS 1.5 mc | IV |
| | TPS, 60 ug and DNA, 10 ug | IV |
| 4/27 | ³H-TPS 1.5 mc | IV |
| 4/29 | ³H-TPS 1.5 mc | IV |
| | TPS, 60 ug and DNA, 10 ug | IV |
| 4/30 | ³H-TPS 1.5 mc | IV |
| 5/3 | ³H-TPS 1.5 mc | IV |
| 5/6 | TPS. 60 ug and DNA, 10 ug | IV |
| 5/14 | TPS. 60 ug and DNA, 10 ug | IV |
| | ³H-TPS 1.5 mc | IV |
| 5/18 | ³H-TPS 0.5 mc | oral |
| 5/23 | ³H-TPS 0.5 mc | oral |
| 5/27 | ³H-TPS 0.5 mc | oral |

By Mar. 14, 1963, the bone looked like new bone had been laid down. Pain was absent in the last days. The patient died on Dec. 19, 1963.

EXAMPLE 30

Ovarian adenocarcinoma

A 64 year old white married woman was found at operation to have a large massive gangrenous adenocarcinoma of the ovaries with metastasis to the omentum. Only part of the tumor was removed. The patient was started on combined oral and parenteral regimen with ³H-TPS (0.029 mc/mg) on May 23, 1963, three days post-surgery, and thereafter did very well.

| Date | Treatment | Administration Route |
|---|---|---|
| 5/23/63 | ³H-TPS 0.5 mc | IV |
| | TPS and DNA, 200 ug each | IV |
| 5/24 | ³H-TPS 1.0 mc | oral |
| 5/25 | ³H-TPS 0.5 mc | oral |
| 5/27 | ³H-TPS 0.5 mc | oral |
| | TPS and DNA, 200 ug each | IV |
| 5/29 | ³H-TPS 0.5 mc | oral |
| 5/31 | ³H-TPS 0.5 mc | oral |

For example, on Jan. 12, 1964 she was reported as doing fine and working "like a horse", and continued so for several years. On May 9, 1970 she was admitted to a hospital and diagnosed as having carcinoma of the small intestines with metastasis. On May 15, 1970 she was discharged to go to a nursing home. Her survival from her original ailment for over seven years is an exceptional occurrence, to which the treatment with ³H-TPS must be accountable.

EXAMPLE 31

Ovarian adenocarcinoma

A 39 year old married woman with marked loss of weight, cachexia, and bed sores over the back area was found at operation to have ovarian adenocarcinoma with metastasis to other abdominal organs. After partial tumor removal, she was given radioactive gold intraperitoneally. Her physician refused to allow her to have the TPS treatment until after an interval of six weeks to see if the gold treatment would help. She lost 37 pounds and was going from bad to worse. On Oct. 27, 1964 she was started on an oral ³H-TPS regimen and injections of TPS and tumor tissue DNA.

| Date | Treatment | Administration Route |
|---|---|---|
| 10/27/64 | ³H-TPS 15 uc | oral |
| | TPS, 10 ug and DNA 20 ug | IV |
| 10/28–11/6 | ³H-TPS 15 uc (daily) | oral |
| 11/9 | ³H-TPS 26 ur | |
| | TPS, 10 ug and DNA, 20 ug | IV |
| 11/10–11/18 | ³H-TPS 26 uc (daily) | oral |
| 11/23 | ³H-TPS 33 ur | |
| | TPS, 10 ug and DNA, 20 ug | IV |
| 11/24–12/2 | ³H-TPS 33 uc (daily) | oral |
| 12/12 | ³H-TPS 45 uc | oral |
| | TPS, 10 ug and DNA, 20 ug | IV |

She regained the 37 pounds of weight and her health, and had resumed normal activities, all of which improvement and regained weight and health was observed by October 1965, which is one year after she was given treatment according to this invention. She resumed her full schedule of activity until October, 1966 (i.e. two years after therapy by the method of this invention) when a recurrence of her disease developed. A second operation revealed metastatic spread in the abdomen. The patient, however, at this time did not wish to take the treatment again. She passed away on Jan. 4, 1967. This two-year period of freedom from disease in such case following the treatment by the method of this invention is certainly exceptional for this particular metastatic tumor, and is indicated to be due in part to the administration of this treatment.

J. Immunoprevention and Immunotherapy in Mice

A controlled study was conducted to determine an effective pre-inoculum treatment schedule for TPS administration. Various combinations of dosages, pre-inoculum treatment, post inoculum treatment and adjuvant were used, with mean survival time as an end point. The treatment schedule is shown in Table 2. For each group, Swiss DC female mice obtained from Charles River Laboratories were used. At day zero, $5 \times 10^6$ sarcoma 180 cells were injected ip into each mouse.

Table 3 shows the data resulting from the study, giving the date of death for individual mice, mean survival time (MST) and the T/C ratio, the latter being an indication of effectiveness of the treatments of Groups 2–7 over the untreated control (Group 1). A T/C value of 100 or greater indicates a prolongation of life.

TABLE 2

| GROUP | CAGE NO. | No. of MICE | AGENT | Dose ug/mouse | Pre-inoculum Treatment Schedule | | | Tumor Implant Day 0 | Post-Inoculum Treatment Schedule Days 0 + 2 hr - 8 |
|---|---|---|---|---|---|---|---|---|---|
| | | | | | -3 Wk Day - 21 | -2 Wk Day - 14 | -1 Wk Day - 7 | | |
| 1 | 1 | 8 | — | — | — | — | — | * | — |
| | 2 | 8 | — | — | — | — | — | * | — |
| | 3 | 8 | — | — | — | — | — | * | — |
| 2 | 4 | 8 | TPS | 3 | — | — | — | * | * |
| | 5 | 8 | TPS | 9 | — | — | — | * | * |
| | 6 | 8 | TPS | 30 | — | — | — | * | * |
| 3 | 7 | 8 | TPS | 3 | * | * | * | * | — |
| | 8 | 8 | TPS | 9 | * | * | * | * | — |
| | 9 | 8 | TPS | 30 | * | * | * | * | — |
| 4 | 10 | 8 | TPS | 3 | * | * | * | * | * |
| | 11 | 8 | TPS | 9 | * | * | * | * | * |
| | 12 | 8 | TPS | 30 | * | * | * | * | * |
| 5 | 13 | 8 | TPS + ADJ | 3 | * | * | * | * | — |
| | 14 | 8 | TPS + ADJ | 9 | * | * | * | * | — |
| | 15 | 8 | TPS + ADJ | 30 | * | * | * | * | — |
| 6 | 16 | 8 | Saline + ADJ | — | * | * | * | * | — |
| 7 | 17 | 8 | Cyclo- | 40 mg/kg | — | — | — | * | * |
| | 18 | 8 | phosphamide | 20 mg/kg | — | — | — | * | * |

— = No treatment.
* = Treatment.

TABLE 3

| GROUP | TREATMENT | Dose ug/mouse | Treatment Schedule Route of Adm. | Vehicle | Δ X Body Wt. Day 0–Day 7 GM | Day of Death - Ind. Mice | | | | | | | | Mean Survival Time | T/C |
|---|---|---|---|---|---|---|---|---|---|---|---|---|---|---|---|
| | | | | | | 1 | 2 | 3 | 4 | 5 | 6 | 7 | 8 | | |
| 1.1 | Untreated | | (see Table 2) | | +4.6 | 11 | 13 | 14 | 15 | 15 | 15 | 16 | 16 | | |
| 1.2 | Control | | | | +4.6 | 10 | 10 | 11 | 14 | 15 | 16 | 16 | 17 | 14.4 | |
| 1.3 | | | | | +4.7 | 11 | 12 | 13 | 13 | 14 | 14 | 15 | 18 | | |
| 2.4 | TPS | 3 | | Saline/Sol. | +2.2 | 9 | 15 | 15 | 17 | 17 | 19 | 20 | 26 | 17.2 | 119 |
| 2.5 | | 9 | | | +3.7 | 9 | 13 | 14 | 14 | 16 | 17 | 22 | 23 | 16.0 | 111 |
| 2.6 | | 30 | | | +3.6 | 10 | 11 | 12 | 13 | 16 | 16 | 17 | | 15.7 | 109 |
| 3.7 | TPS | 3 | | Saline/Sol. | +4.8 | 10 | 11 | 13 | 14 | 15 | 15 | 15 | 16 | 14.7 | 102 |
| 3.8 | | 9 | | | +5.3 | 14 | 15 | 15 | 15 | 16 | 16 | 16 | 16 | 15.6 | 108 |
| 3.9 | | 30 | | | +4.2 | 12 | 12 | 14 | 14 | 15 | 16 | 16 | 16 | 15.0 | 104 |
| 4.10 | TPS | 3 | | Saline/Sol. | +2.3 | 10 | 13 | 15 | 15 | 16 | 17 | 18 | 18 | 16.0 | 111 |
| 4.11 | | 9 | | | +3.0 | 9 | 9 | 15 | 15 | 16 | 16 | 17 | 17 | 15.7 | 109 |
| 4.12 | | 30 | | | +4.2 | 11 | 11 | 11 | 15 | 15 | 16 | 16 | 16 | 15.2 | 106 |

TABLE 3-continued

| GROUP | TREATMENT | Dose ug/mouse | Treatment Schedule Route of Adm. | Vehicle | Δ X Body Wt. Day 0–Day 7 GM | Day of Death - Ind. Mice | | | | | | | | Mean Survival Time | T/C |
|---|---|---|---|---|---|---|---|---|---|---|---|---|---|---|---|
| | | | | | | 1 | 2 | 3 | 4 | 5 | 6 | 7 | 8 | | |
| 5.13 | TPS + ADJ | 3 | | Saline/Susp. | +4.3 | 6 | 6 | 7 | 11 | 12 | 14 | 23 | 33 | 12.0 | 83 |
| 5.14 | | 9 | | | +1.5 | 8 | 9 | 9 | 9 | 9 | 11 | 12 | 14 | 9.4 | 65 |
| 5.15 | | 30 | | | +4.6 | 6 | 9 | 10 | 13 | 14 | 15 | 26 | | 14.0 | 97 |
| 6.16 | Saline + ADJ | | | Saline/Susp. | +1.7 | 9 | 9 | 9 | 10 | 10 | 12 | 16 | 29 | 10.2 | 71 |
| 7.17 | Cyclophosphamide | 40* | | Saline/Sol. | +3.0 | 14 | 15 | 16 | 16 | 16 | 17 | 17 | 19 | 16.3 | 113 |
| 7.18 | | 20* | | | +4.7 | 16 | 16 | 16 | 16 | 17 | 17 | 17 | 18 | 16.7 | 116 |

Comments:
*mg/kg/inj.

TABLE 4

| GROUP | | % ALIVE | | | | | |
|---|---|---|---|---|---|---|---|
| | | DAY 17 | DAY 20 | DAY 23 | DAY 26 | DAY 29 | DAY 32 |
| Controls | Gr. 1 | 0/8 (0%) | 0 | | | | |
| | Gr. 1.2 | 1/8 (12%) | 0 | | | | |
| | Gr. 1.3 | 1/8 (12%) | 0 | | | | |
| Therapy | Gr. 2.4 | 5/8 (62%) | 2/8 (25%) | 1/8 (12%) | 1/8 (12%) | 0/8 | 0/8 |
| (TPS Alone) | Gr. 2.5 | 3/8 (37%) | 2/8 (25%) | 1/8 (12%) | 0/8 | 0/8 | 0/8 |
| | Gr. 2.6 | 2/8 (25%) | 1/8 (12%) | 1/8 (12%) | 1/8 (12%) | 1/8 (12%) | 1/8 (12%)** |
| Prevention | Gr. 3.7 | 0/8 (0%) | 0 | | | | |
| (TPS Alone) | Gr. 3.8 | 0/8 (0%) | 0 | | | | |
| | Gr. 3.9 | 0/8 (0%) | 0 | | | | |
| Therapy and Prevention | Gr. 4.10 | 3/8 (37%) | 0 | | | | |
| | Gr. 4.11 | 2/8 (25%) | 0 | | | | |
| (TPS Alone - Before and After) | Gr. 4.12 | 0/8 (0%) | 0 | | | | |
| Prevention | Gr. 5.13 | 2/8 (25%) | 2/8 (25%) | 2/8 (25%) | 1/8 (12%) | 1/8 (12%) | 1/8 (12%)* |
| (TPS c Adjuvants - Alone) | Gr. 5.14 | 0/8 (0%) | 0/8 | 0/8 | 0/8 | 0/8 | 0/8 |
| | Gr. 5.15 | 2/8 (25%) | 2/8 (25%) | 2/8 (25%) | 2/8 (25%) | 1/8 (12%) | 1/8 (12%)** |
| Saline c Adjuvants | Gr. 6 | 1/8 (12%) | 1/8 (12%) | 1/8 (12%) | 1/8 (12%) | 1/8 (12%) | 0 |
| Therapy Cyclophosphamide | Gr. 7.17 | 3/8 (37%) | 0 | | | | |
| | Gr. 7.18 | 4/8 (50%) | 0 | | | | |

**Still alive on day 33 (Cures).
*died by day 32.

Conversely, a T/C ratio of less 100 indicates a life shortening with the use of the corresponding treatment.

Table 4 shows survival for each group, not compared to controls, in terms of percentage of each group living after a given number of days.

The TPS-dial-LPS also is applicable relatively similarly in immuno-prophylaxis and immuno-therapy. So also is the lipopolysaccharide derived from malignant tumor tissue (and briefly designated TLPS). So far as presently indicated, the best way to administer the TLPS also is intradermally. Either of TLPS and TPS-dial-LPS can be used in immuno-prophylaxis in 0.1 ml. doses in the dilutions indicated for TPS-dial-LPS (Section F above) from 2 to 3 times weekly. For immuno-therapy the TLPS can be used in about the same doses and dosage regimen as recited above for TPS-dial-LPS.

Incidentally, consistency in potency comparison test results show that the TPS derived from tissue cultures infected with the GA strain of leucosis virus to be identical in potency with the TPS derived from livers of chickens sick with leucosis from the same strain. This presents the novel use of tissue cultures as a source for preparing TPS, for example, by the method illustrated in Sections A and B above, for use in immunization as by the methods and in the applications disclosed herein.

The LPS derived from a pathogenic or pyrogenic bacterial source, when dry (as by lyophilization) is a white, fluffy, non-hydroscopic, water-soluble solid having a molecular weight in the range of about 2.3 million to 4.7 million, on being dissolved in water at 1 mg. per ml. gives a faintly hazy solution; and is inert to formaldehyde and to aqueous phenol solutions, e.g. containing about 45% phenol, and stable to such concentration phenol solution at elevated temperature of from about 10 to about 70° C.; and is insoluble in acetone and in chloroform, is precipitated from water by admixing acetone in it, is substantially entirely protein-free, contains from about 0.8 to 4% of ribonucleic acid; and when injected intravenously in a rabbit's ear at a level of as little as 75 nanograms per kilogram of body weight gives a pyrogenic response (i.e. produces fever).

The TLPS derived from malignant tumor tissue has the properties given just above for the bacterial source LPS, but lacks its pyrogenic response.

'Freon 113' is dichloro-monofluoro, monochlorodifluoro ethane. The isolation of the DNA from the disintegrated tumor tissue is not limited to use of 'Freon 113' for any equivalent for it such as 'Freon-114B2' which is di-(monobromodifluoro)-ethane, can be used similarly.

While the invention has been explained by detailed description of certain specific embodiments of it, it is understood that various modifications and/or substitutions can be made in any of them within the scope of the appended claims which are intended also to cover equivalents of any of them.

What is claimed is:

1. A method of enhancing the defense mechanisms of the body of a mammal against either or each of malignant tumor incipience and such tumor development, which method comprises administering to said mammal a tumor-antibody-stimulating effective dosage of
  (a) the tritiated form of a glyco-protein-polysaccharide-like antigenic substance derived from cancerous tissue and which disperses readily and is stable in cold to boiling water and in aqueous solution, non-dialyzable at a molecular weight cut-off point of 3500, inert to alkali and to isotonic phosphate buffered saline solution, precipitated from aqueous medium by isopropanol and insoluble in isopropanol ether, chloroform, and butanol, gives a positive Molisch test and negative Dische test, and on hydrolysis with dilute sulfuric acid at about 100° C., followed by deionization, yields a hydrolysate containing identifiable sugars, and on finite analysis shows trace amounts of amino acids typical of N-glycoproteins; which substance when in an aqueous vehicle and on therein being admixed with blood serum yields a preparation which when injected intra-dermally into a subject to be tested, produces an erythema about the injection site; and
  (b) malignant tumor-derived deoxyribonucleic acid; at an adequate regimen, to develop an improved level of defense against either or each of said malignant tumor incipience and development.

2. A method of enhancing the defence mechanisms of the body of a mammal bearing a malignant tumor against development of said malignant tumor, which method comprises administering to said mammal a tumor-antibody-stimulating effective dosage, of
  (a) the tritiated form of a glycoprotein-poly-saccharide-like antigenic substance derived from cancerous tissue and which disperses readily and is stable in cold to boiling water and in aqueous saline solution, non-dialyzable at a molecular weight cut-off point of 3500, inert to alkali and to isotonic phosphate buffered saline solution, precipitated from aqueous medium by isopropanol and insoluble in isopropanol ether, chloroform, and butanol, gives a positive Molisch test and negative Dische test, and on hydrolysis with dilute sulfuric acid at about 100° C., followed by ionization, yields a hydrolysate containing identifiable sugars, and on finite analysis shows trace amounts of amino acids typical of N-glycoproteins; which substance when in an aqueous vehicle and on therein being admixed with blood serum yields a preparation which when injected intra-dermally into a subject to be tested, produces an erythema about the injection site; and
  (b) malignant tumor-derived deoxyribonucleic acid; at an effective regimen, to develop an improved level of defense against said malignant tumor development.

3. The method of claim 2, wherein there is also administered the non-tritiated form of said antigenic substance of (a).

* * * * *